US006939566B2

(12) United States Patent
Batarseh et al.

(10) Patent No.: US 6,939,566 B2
(45) Date of Patent: Sep. 6, 2005

(54) MICROBICIDAL FORMULATIONS AND METHODS TO CONTROL MICROORGANISMS

(76) Inventors: Kareem I. Batarseh, 8610 Larkview La., Fairfax Station, VA (US) 22039; Marwan Al-Kayed, P.O. Box 18, Naur (JO)

(*) Notice: Subject to any disclaimer, the term of this patent is extended or adjusted under 35 U.S.C. 154(b) by 77 days.

(21) Appl. No.: 09/761,561

(22) Filed: Jan. 17, 2001

(65) Prior Publication Data

US 2003/0035848 A1 Feb. 20, 2003

Related U.S. Application Data

(63) Continuation-in-part of application No. 09/294,143, filed on Apr. 20, 1999, now Pat. No. 6,242,009, and a continuation-in-part of application No. PCT/US00/10665, filed on Apr. 20, 1999.

(51) Int. Cl.$^7$ .......................... A01N 59/00; A01N 33/00
(52) U.S. Cl. ...................... 424/618; 424/613; 424/614; 424/616; 424/617; 424/620; 424/621; 424/622; 424/625; 424/626; 424/627; 424/629; 424/630; 424/638; 424/639; 424/641; 424/644; 424/646; 424/649; 424/650; 424/652; 424/654; 424/655; 424/682; 424/702; 424/DIG. 6; 514/492; 514/493; 514/494; 514/495; 514/497; 514/498; 514/499; 514/500; 514/501; 514/504; 514/505; 514/553; 514/554; 514/557; 514/561; 514/635; 514/706; 514/714; 514/724
(58) Field of Search ................................ 424/618, 613, 424/614, 616, 617, 620, 621, 622, 625, 626, 627, 629, 630, 638, 639, 644, 641, 646, 649, 650, 652, 654, 655, 682, 702; 514/492, 493, 494, 495, 497, 498, 499, 500, 501, 504, 505, 553, 554, 557, 561, 635, 706, 714, 724

(56) References Cited

U.S. PATENT DOCUMENTS

| | | | |
|---|---|---|---|
| 3,422,183 A | 1/1969 | Ellison | 424/28 |
| 4,337,269 A | 6/1982 | Berke et al. | 514/494 |
| 4,396,413 A | 8/1983 | Miller et al. | 71/67 |
| 4,425,325 A | 1/1984 | Ritchey et al. | 424/54 |
| 4,758,439 A | 7/1988 | Godfrey | 426/74 |
| 4,830,716 A | 5/1989 | Ashmead | 204/72 |
| 4,847,049 A | 7/1989 | Yamamoto | 422/24 |
| 4,915,955 A | 4/1990 | Gomori | 424/616 |
| 5,342,846 A | 8/1994 | Singh et al. | 514/312 |
| 5,389,360 A | 2/1995 | Mobley et al. | 424/49 |
| 5,504,055 A | 4/1996 | Hsu | 504/121 |
| 5,510,315 A | 4/1996 | Kurotsu et al. | 504/115 |
| 5,516,480 A | 5/1996 | Krall et al. | 264/343 |
| 5,516,925 A | 5/1996 | Pedersen et al. | 556/50 |
| 5,616,251 A | 4/1997 | Batarseh | 210/725 |
| 5,708,023 A | 1/1998 | Modak et al. | 514/494 |
| 5,710,252 A | 1/1998 | Weber et al. | 530/356 |
| 6,242,009 B1 | 6/2001 | Bataresh et al. | 424/618 |

FOREIGN PATENT DOCUMENTS

| | | |
|---|---|---|
| DE | 1 642 001 | 4/1971 |
| EP | 0 041 792 | 5/1981 |
| FR | 2 728 143 | 12/1994 |
| JP | 07138167 | 5/1995 |
| JP | 1998 0186163 | 1/1998 |
| JP | 10338605 | 12/1998 |
| JP | 11-209209 | 3/1999 |
| JP | 016905 | 1/2000 |
| WO | WO 94/04167 | 3/1994 |
| WO | WO 95/13700 | 5/1995 |
| WO | WO 96/01231 | 1/1996 |
| WO | WO 97/02038 | 1/1997 |
| WO | WO 97/30057 | 8/1997 |
| WO | WO 97/33477 | 9/1997 |
| WO | WO 99/17735 | 4/1999 |
| WO | WO 00/62618 | 2/2000 |
| WO | WO 00/27390 | 5/2000 |

OTHER PUBLICATIONS

Poddymov et al., Formation of Complexes Between (Ag(I) and Several Amino Acids, Zh.Neorg. Khim. (1977), 22(6), 1617–20 (English Translation).*
Sanchez et al., Comparative Potentiometric Determination of the Stability Constants of Silver (I) with alpha–Alanine, DL–Phenylalanine, and DL–Serine, Analusis (1981), 9(9), 455–8 (English Translation).*
Poddymov et al., Study of the complexing of silver (1) with some amino acids. ZH. Neorg. Khim. 1997, vol. 22, No. 6, pp. 1617–1620.

(Continued)

*Primary Examiner*—S. Mark Clardy
*Assistant Examiner*—Frank Choi
(74) *Attorney, Agent, or Firm*—Kilyk & Bowersox, P.L.LC.

(57) ABSTRACT

Microbicidal formulations are described which are preferably ecologically friendly and non-toxic to mammals, and are highly effective against a broad spectrum of detrimental pathogenic microorganisms. The microbicidal formulation contains complexes having the formula R-M, wherein R is at least one organic chelating moiety and M is at least one metal ion which is microbicidal to at least one microorganism. These complexes can disrupt microorganism activities by penetrating the natural protecting bio-films of such microorganisms through the reaction of the R-group with the organic constituents of these microorganisms while releasing M into their intra-cellular media. Thus, this process exhibits its biocidal activities from the inside-out, contrary to other methods which rely on damaging the protective biofilms. These microbicidal formulations can be diluted in suitable proportions into aqueous systems to produce the desired dosages for each individual case, depending on the level and the severity of the contamination. The microbicidal formulations can be applied by conventional methods, e.g., spraying, soaking, fogging, impregnation, and the like. The formulations can also be used as preservatives, such as for fresh or cut flowers and plants. These microbiocides can also be made as gel or solids in different forms by using techniques available to those skilled in the art.

27 Claims, 4 Drawing Sheets

OTHER PUBLICATIONS

Sanchez et al., Potentiometric determination of silver complexes stability constants: alpha.–alanine, DL–phenylalanine and DL–serine. Analusis, 1981, vol. 9, No. 9, pp. 455–458.

Tzeng et al., "Products in light–mediated reactions of free methionine–riboflavin mixtures that are biocidal to micro-organisms", (Can. J. Microbiol. vol. 36, No. (7), pp. 500–506), STN/CAS, Caplus, Abstract, 1990.

Castillo et al., "Synthesis and spectral properties of new complexes between glycine and titanium (III), vanadium(III), chromium(III), iron(III), cobalt(II), nickel(II) and copper(II)" (Transition Met. Chem. (Weinheim, Ger.)(1984), 9(7),268–70), STN online, file.

M'Hiri et al., "Physicochemical and structural study of metal complexes of L–.beta.–phenylalanine" (J. Soc. Chim. Tunis. (1983), 9, 19–33), STN online, file CAPLUS, Abstract.

Saxena et al., "Electrometric study of divalent zinc, cadmium and mercury complexes of DL–tryptophan" (Trans. SAEST (1981), (1), 45–8), STN online, file CAPLUS, Abstract.

Cusack et al. "Synthesis, Moessbauer and infrared studies of inorganic tin derivatives of amino acids" (Inorg. Chim. Acta (1980), 46 (4), L73–L75), STN online, filed HCAPLUS, Abstract.

Mogilevkina et al., "Antitumor activity of complexes of platinum with acids and peptides" (Onkologiya (Kiev) (1979), 14–40–3), STN online, file HCAPLUS, Abstract.

Volshtein et al., "Complexes of platinum (II) with .beta.–phenyl–.alpha.–alanine" (Zh. Neorg. Khim (1975), 20(12), 3352–6), STN online, file CAPLUS, Abstract.

Kollmann et al., "Preparation and characterization of some amino acid and peptide complexes of gold (I,III), palladium(II), and platinum(II)" (J. Prakt. Chem. (1975), 317(3), 515–19), STN online, file HCAPLUS, Abstract.

Natusch et al., "Direct detection of mercury (II)–thio–ether bonding in complexes of methionine and S–methylcysteine by 1H nuclear magnetic resonance" (J. Chem. Soc. D (1970), (10), 596–7), STN online, file HCAPLUS, Abstract.

Volshtein et al., "Methionine as a tridentate ligand in platinum(II) complexes" (Dokl. Akad. Nauk SSSR (1968), 178(3), 595–7), STN online, file HCAPLUS, Abstract.

Perrin et al., "Histidine complexes with some bivalent cations" (J. Chem. Soc. A (1967), (5), 724–8), STN online, file HCAPLUS, Abstract.

Fromont, M. et al., "Influence du Tartrate Double de Sodium et de Potassium sur la Croissance des Depots Electrolytiques D'argent Obtenus a Partir d'une Solution Aqueuse de Nitrate" Comptes Rendus de L'academie des Science, Paris, t271C, pp. 253–256 (1970).

Sumarokova et al., "Interaction of tine dichloride with organic bases" (Teor. Rastvorov (1971) 323–9), STN online, file CAPLUS, Abstract.

Simeon et al., "Chelation of some bivalent metal ions with alanine and phenylalanine", (Croat. Chem. Acta (1966) 38, 161–7), STN online, File HCAPLUS, Abstract.

Khurshid, "Antibacterial activity of iron(II) and zinc(II)–amino acid complexes" (Pak. J. Pharmacol. (1996), 13(1), 41–45), STN online, file HCAPLUS, Abstract.

Ali–Mohamed et al. "Studies on the bacterial activity of cobalt(III), complexes. Part II. Cobalt (III) aminoacidato–complexes" (Transition Met. Chem. (London) (1989), 14 (3), 181–4), STN online, file HCAPLUS, Abstract.

Kawada et al., "Methionine and pentocystine copper salts as bactericides and fungicides" (1974, JP 49012028), STN online, file HCAPLUS, Abstract.

Yoshida et al., "Methionine zinc salt for the control of Alternaria mali" (1976, JP 51112517), STN online, file HCAPLUS, Abstract.

Tumanov et al., "Antimicrobial activity of copper (II) coordination compounds with .alpha.–amino acids" (Izv. Akad. Nauk Mold. SSR, Ser. Biol. Khim. Nauk (1983), (6), 44–6), STN online, file HCAPLUS, Abstract.

Ackermann et al., "Preparation of substituted phenylalanine– metal complexes having fungicidal activity" (1989, DD 267731), STN online, file HCAPLUS, Abstract.

Jain et al., "Some new metal chelates of L–lysine monohydrochloride as potential antifungals" (Indian J. Phys. Nat. Sci. (1983), 3(A), 51–2), STN online, file HCAPLUS, Abstract.

Van Nostrand's Scientific Encyclopedia ($8^{th}$ Ed. 1995), pp. 618, 619.

Goodman and Gilman's, The Pharmacological Basis of Therapeutics ($7^{th}$ Ed. 1985), pp. 962, 963, 968.

Ohtaki et al., "A potentiometric study on complex formation of silver(I) ion with glycine and beta–alanine in aqueous solution", Bull. Chem. Soc. Jpn., vol. 53 (1980), pp. 2865–2867.

Gowda et al., "Interaction of acidic amino acids with bivalent metal ions," J. Electrochem. Soc. India., vol. 30, No. 4 (1981), pp. 336–340.

Brady, et al. General Chemistry Principles and Structure (Third Edition), Chapter 4, pp. 126 and 127, 1982.

Menabue, et al., "Silver(I) Complexes with N–Protected Amino Acids", Inorganic Chimica Acta, 46, (1980) L77–L78.

John R.J. Sorenson, "Copper Chelates as Possible Active Forms of the Antiarthritic Agents", Journal of Medical Chemistry, 1976, vol. 19, No. 1, pp. 135–148.

* cited by examiner

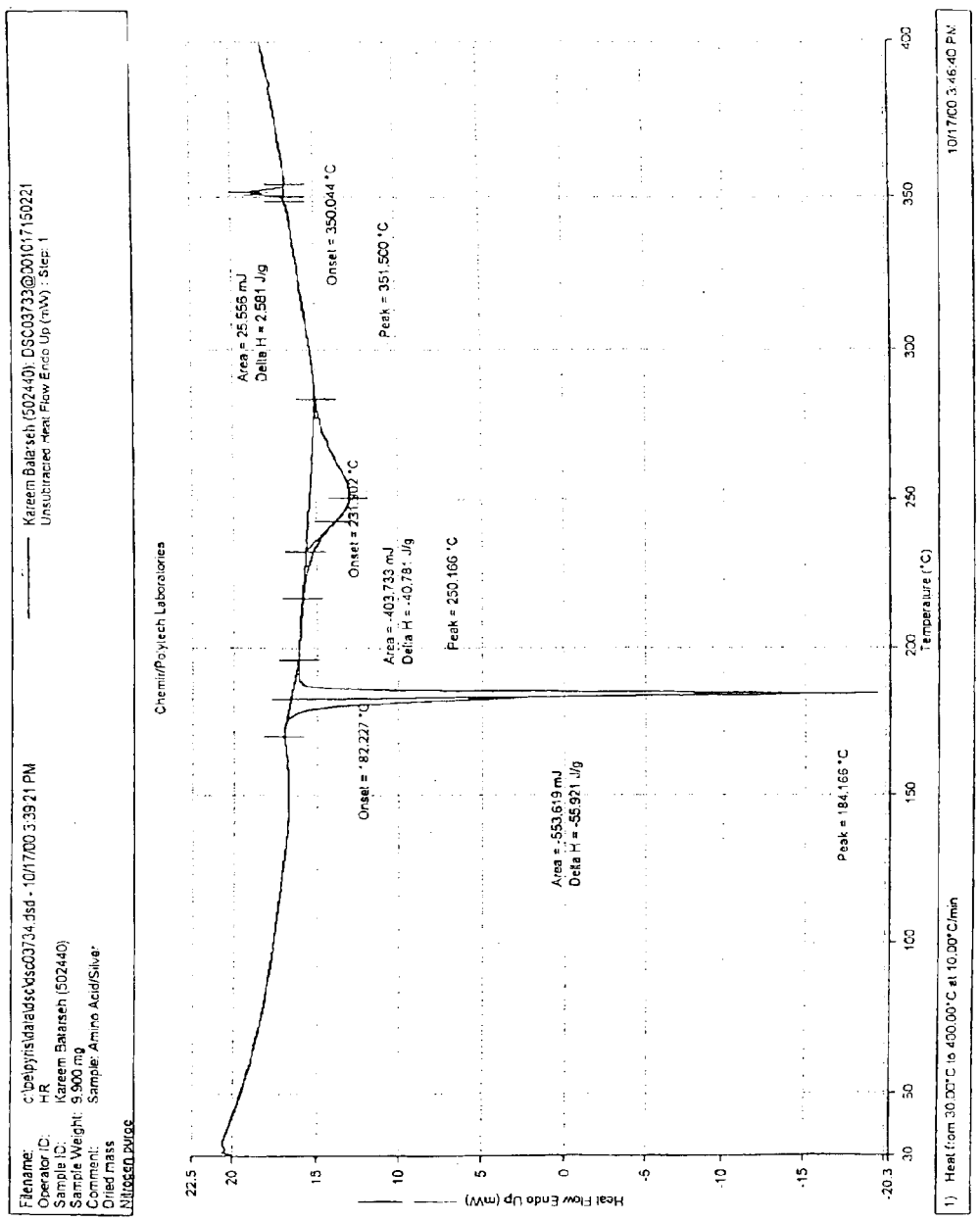
Figure 1. DSC Spectrum

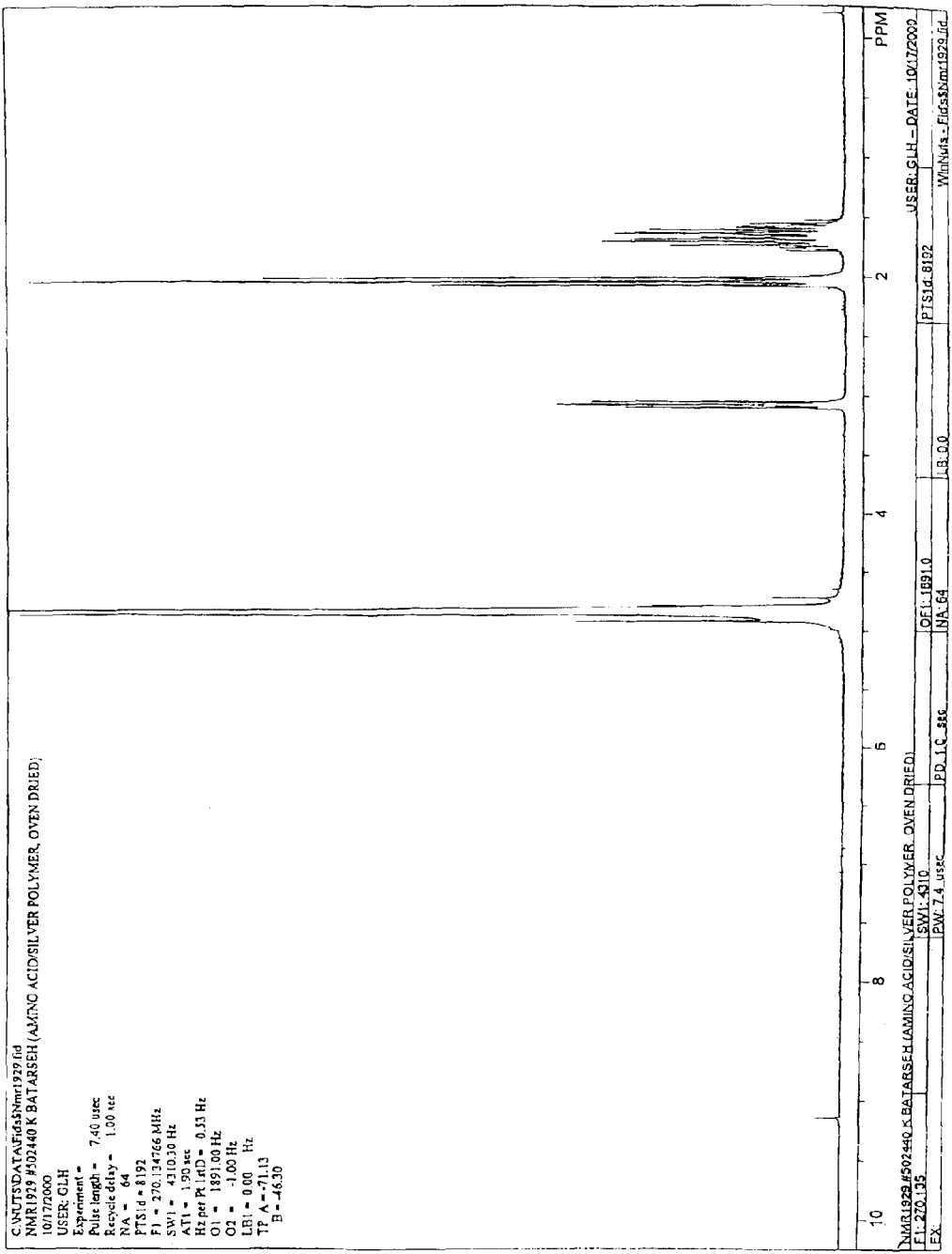
Figure 2. Proton NMR Spectrum

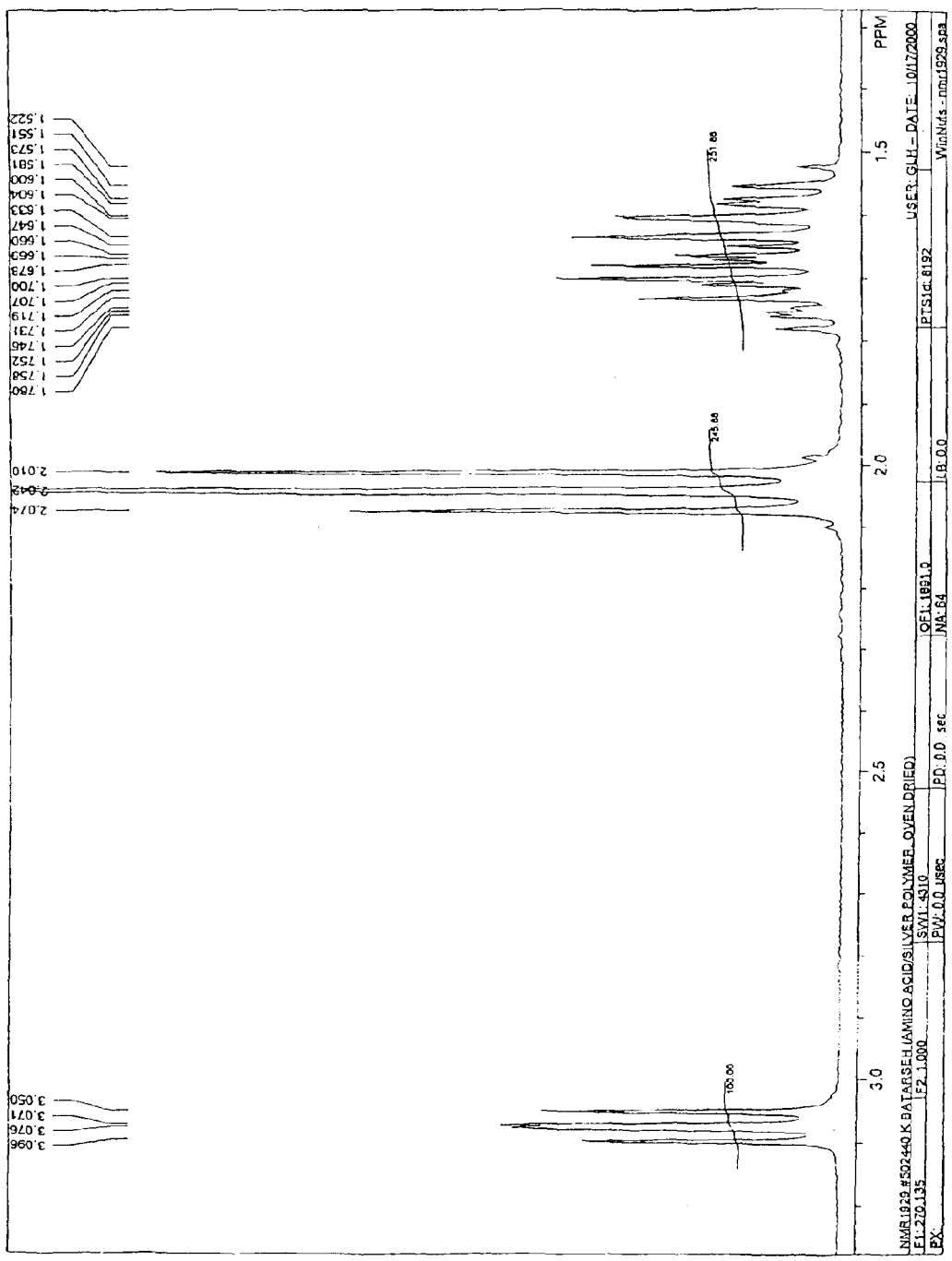
Figure 2. Proton NMR Spectrum – Cont.

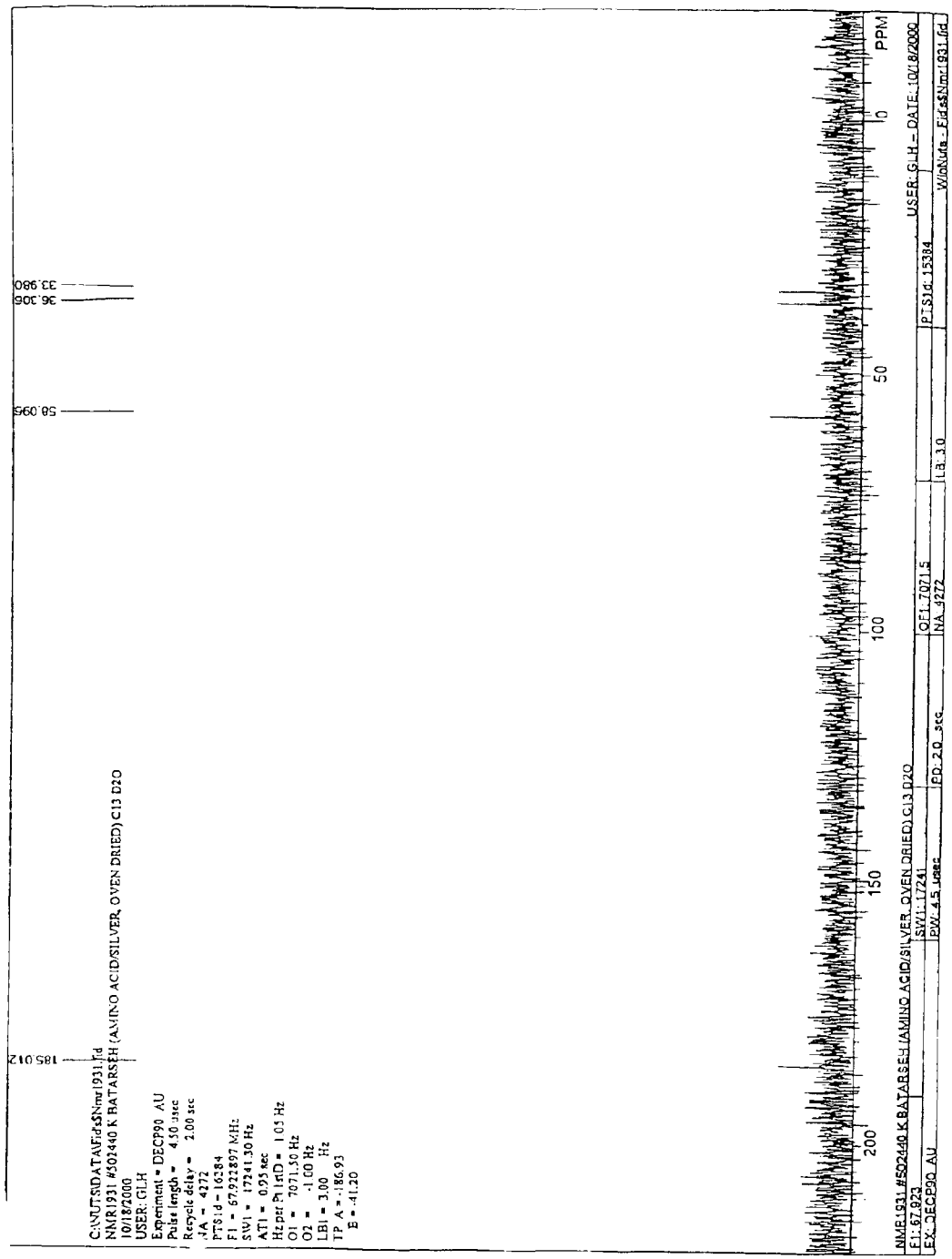
Figure 3. Carbon NMR Spectrum

MICROBICIDAL FORMULATIONS AND METHODS TO CONTROL MICROORGANISMS

CROSS REFERENCE TO RELATED APPLICATIONS

This application is a continuation-in-part of U.S. patent application Ser. No. 09/294,143, filed Apr. 20, 1999 now U.S. Pat. No. 6,242,009, and also is a continuation-in-part of International Patent Application No. PCT/US00/10665 filed Apr. 20, 1999, both incorporated herein in their entirety by reference.

FIELD OF THE INVENTION

The present invention relates in general to controlling microorganisms and more particularly relates to microbicides which are preferably environmentally friendly and non-toxic to mammals and which are highly effective against viruses, amoebea, bacteria (both gram-negative and-positive), fungi, algae, spores, and the like. The present invention specifically relates to organo-metallic microbicidal formulations; their microbicidal applications, and methods of preparation.

BACKGROUND OF THE INVENTION

Water is the most important element of life since it comprises almost 80% of the human body. In addition, food hygiene depends solely on water, and therefore contamination of water is a common vehicle for the transport of epidemic diseases to humans like Typhoid, food poisoning, and Dysentery. For example, Psychrophilic bacteria's presence in the micro-flora in water can affect refrigerated food and spoil it. Hence, water contamination cannot be overlooked and extreme measures should be taken to assure a high quality of water to sustain life.

With the advent of technology, clean water is becoming a scarce commodity. Water contamination is unequivocally becoming a worldwide problem with unknown ramifications, and billions of U.S. dollars are spent annually to improve its quality. Contamination of waters is not only restricted to industrialized countries, but includes developing nations as well. Therefore, there is an immediate need to find poignant solutions to maintain and preserve water sources.

Recently, there has been a growing interest among scientists and engineers to develop new water and food disinfectant technologies to clean water from dangerous microorganisms. Various methods have been employed which are divided into two categories; namely, physical, chemical, or both. The physical category is represented by techniques utilizing ultrafiltration, reverse osmosis, radiation, freezing, heating, and ultrasound. Although these methods have proved to be effective, the drawbacks include the large electricity requirements and expensive equipment. On the other hand, the chemical category relies on the use of chemical adjuvants which exhibit biocidal properties such as aldehydes, phenols, alcohol, potassium permanganate, and chlorine and certain chlorine containing compounds. Some of these chemicals have many disadvantages associated with them and are now considered poisonous compounds. For instance, people coming into contact with these substances can develop skin irritation and suffer from long time illnesses which in some cases can be fatal; not to mention the unpleasant taste and odor associated with these chemicals. In addition, formation of mutagenic and carcinogenic agents, and genetic resistance are also some of their disadvantages. Notwithstanding, such compounds have afforded a way to battle these harmful microorganisms and their effectiveness have been unequivocally demonstrated.

Other methods have relied upon the use of ultra-violet irradiated silver fluoride solutions containing silver as a source of germicide activities, such as U.S. Pat. No. 3,422,183, incorporated herein in its entirety by reference. However, such techniques require expensive equipment and large amounts of electricity.

Hydrogen peroxide is a strong oxidizing agent, and it has been used for the past 40 years as a disinfectant. Its main advantage is that it does not produce toxic residue or by-products. It has been used ubiquitously as an indirect food additive, as a disinfectant in hospitals, as a decontamination and purification agent of industrial waste water, and as a cleaning agent for exhaust air. Nonetheless, it decomposes readily to form water and oxygen, and has high sensitivity to sunlight and UV rays. Therefore, it is not suited for long-term use since recontamination cannot be circumvented.

In 1880, the Swiss botanist Carl van Nageli observed that highly diluted silver solutions have an algicidal effect. To describe this effect he coined the term "Oligodynamic". Colloidal silver, which is a pure, all-natural substance consisting of sub-microscopic clusters of silver ions held in suspension in de-ionized water by tiny positive charges on the silver ions, is a powerful prophylactic antibiotic which was used for years with no known side effects. It acts as an inhibitor disabling particular enzymes which bacteria, fungi, and viruses used in their mode of metabolism.

Based on this oligodynamic property, U.S. Pat. No. 4,915,955, incorporated in its entirety herein by reference, combines the germicidal effects of hydrogen peroxide with silver, an inorganic acid, and an organic stabilizer at concentrations of 10–35 mg/l against many forms of bacteria and viruses. The process is based on silver ions, with the aid of hydrogen peroxide, damaging the protective biofilms of these microorganisms. Hence, this method depends solely on killing germs intercellularly. Accordingly, there is a need to develop a new generation of microbicidal agents that overcome one or more of the above-described disadvantages.

SUMMARY OF THE INVENTION

The present invention relies on using metal ions (M). A chemical matrix or complex is formed wherein these metal ions are attached to an organic-chelating moiety (R), to be used in stoichiometric amounts or more to form complexes, which serves as carriers for M into the intra-cellular medium of such microorganisms. These concentrated complexes can then be mixed with water to form suitable disinfectants. This process is different from previous methods found in the literature where the metal ion remains freely suspended in solution.

A particularly useful application of the disinfectant of the present invention is in the preservation of flowers and plants, as a general disinfectant, sterilization of articles and surfaces and areas, including, but not limited to, food, liquids, (e.g., water, beverages), animal feed, pharmaceuticals, hospitals, surgical equipment, swimming pools, saunas, fish, poultry, cattle, and other farming uses, and the like.

It is to be understood that the preceding general discussion and the discussion which follows are considered explanatory and exemplary in nature, and are solely intended to give additional merits of the current invention, as claimed.

DESCRIPTION OF THE FIGURES

FIG. 1 is a differential scanning calorimetry spectrum of a silver-glutamic acid organo metallic complex of the present invention.

FIG. 2 is a proton NMR spectrum of the silver-glutamic acid organo-metallic complex of the present invention.

FIG. 3 is a carbon NMR organo-metallic complex of the present invention.

The present invention may be more fully understood with reference to the accompanying figures. The figures, which are incorporated in and constitute a part of this specification describe the physical properties of an embodiment of the present invention and together with the description, serve to explain the principles of the present invention.

DETAILED DESCRIPTION OF THE PRESENT INVENTION

The present invention provides a suitable concentrate of organo-metal compounds that form suitable disinfectants upon admixing with water or other aqueous sources. The basic principle that governs the formation of such a concentrate is the fact that the metal ions are attached to an organic-chelating R group used in stoichiometric amounts or more that forms organic complexes. These organic complexes can penetrate the protective biofilms of germs and other microorganisms. Once the R-M complex is inside the biofilm, it can then exhibit its germicidal or biocidal effects by releasing M into their intra-cellular media and, hence, disrupt microbial activities. In the most general terms, this scenario can be depicted as giving these germs a "poisonous pill." Thus, unlike other methods which attribute their biocidal effects through damaging the protective biofilms (from the outside-in, i.e., inter-cellularly), the present invention does the opposite; specifically, killing microorganisms from the inside-out, i.e., intracellularly.

To enhance its activity, the concentrated organic complex can be mixed with other disinfectants, including, but not limited to, isopropanol, chlorhexidine gluconate, chlorhexidine digluconate, chlorhexidine dihydrochloride, chlorhexidine diacetate, and/or hydrogen peroxide, though it is not necessary. In addition, natural and artificial color and flavor additives as well as other additives can be added as well.

Of course, the microbicidal formulations of the present invention can be used either directly, by introduction to a system, e.g., a swimming pool, or can be diluted with aqueous solutions, like distilled and/or deionized water to provide the necessary biocidal activity, depending on the application.

With respect to the organic complex, R-M, the R group is an organic group which can complex with one or more metal ions, and is preferably a group which is amphoteric. Also, the R group is preferably of a chemical nature which microorganisms would find nurishable. Preferably, the R group includes at least one amino acid or can be formed from at least one amino acid.

The amino acids are preferably amphoteric, that is, they can react either as acids or as bases, depending on the circumstances. They exist primarily as neutral dipolar ions or zwitterions ($Z=H_3N^+$—CRH—COO$^-$). Hence, at low pH, the zwitterions exist as cations, and at high pH they exist as anions; therefore at a certain pH, the amino acids preferably exist primarily as zwitterions. This point is called the isoelectric point which depends on the structure of the given amino acid. Primary, secondary, or tertiary amines can all be used here as long as the amine is compatible with (M) in the formation of the complex. The amino acids are preferably chosen so as to make use of the lone pair of electrons on the nitrogen atom where the metal ions (the Lewis acid, electron pair acceptor) can form dative covalent bonds (also known as a coordinate covalent bond) with the carboxylic group of the amino acid. In essence, these metal ions, or Lewis acids, can share an electron pair donated by the amino acid, that is, the ligand, or Lewis base. Preferably, the double bonded oxygen of the carboxylic group of the amino acid is complexed (or forms a dative covalent bond with the double bonded oxygen) to the metal (M), and not to the hydroxy group of the carboxylic group of the amino acid. This is preferably accomplished by forming the complex under low pH conditions (e.g., acidic conditions) and preferably at pH conditions of pH 2.0 or less and more preferably at a pH 1.5 or less.

Preferably, examples of amino acids or compounds containing amino acids which can be used as the R group or to form the R group include, but are not limited to, α-amino acids. Specific examples include, but are not limited to, isoleucine, phenylalanine, leucine, lysine, methionine, threonine, tryptophan, valine, alanine, glycine, arginine, histidine, hydroxyproline, α-aminobutyric acid, asparagine, aspartic acid, cysteine, glutamic acid, glutamine, pherylalanine, proline, serine, tyrosine, and derivatives thereof and mixtures thereof.

With respect to the other part of the complex which is M, M represents at least one monovalent or polyvalent metal ion or cation, which is microbicidal to at least one microorganism. Preferably, the metal ion is microbicidal to a multitude of microorganisms. Examples of the metal ion include, but are not limited to, cations of silver including colloidal silver, copper, zinc, mercury, manganese, chromium, nickel, cadmium, arsenic, cobalt, aluminum, lead, selenium, platinum, gold, titanium, tin, barium, bismuth, vanadium, iron, strontium, antimony, and the like. More than one type of R group and more than one type of M can be used to form the R-M complex, also, mixtures of different R-M complexes can also be used.

The composition provided here may be prepared from various complexes that may form together a more complicated complex and/or complexes. The aqueous solution obtained may be concentrated and dried, and the concentrate can be made as a gel or solid in different forms using conventional methods available to those skilled in the art.

The complex of the present invention can be prepared by forming the metal ion from at least one metal salt compound and the organic chelating moiety from at least one organic compound which is preferably at least one amino acid. In the preferred process of making the organic complex of the present invention, a metal salt compound is mixed with at least one inorganic acid preferably at room temperature (e.g., about 20° C. to about 30° C.) and preferably in the presence of an aqueous solution like a distilled and deionized water. Then, at least an equimolar basis of the organic containing compound such as an amino acid is added to form the metal complex preferably while homogenizing the mixture. This preparation preferably occurs under low pH conditions, such as pH of about 2.0 or less and more preferably at a pH of 1.5 or less. The resulting solution can then be further diluted with aqueous solution and preferably distilled and deionized water and further disinfectants or other additives can be added to form the microbicidal compositions of the present invention. Other parameters can vary, such as the temperature for preparation purposes.

According to the present invention, controlling the growth of at least one microorganism includes both the reduction and/or prevention of such growth. It is to be further understood that by "controlling," the growth of at least one microorganism is inhibited. In other words, there is no growth or substantially no growth of at least one microorganism. "Controlling" the growth of at least one microorganism includes maintaining a microorganism population at a desired level (including undetectable levels such as zero population), reducing a microorganism population to a desired level, and/or inhibiting or slowing the growth of at least one microorganism. Thus, materials and mediums susceptible to attack by at least one microorganism are preserved and/or protected from this attack and the resultant deleterious effects. The present invention also provides a method for controlling the growth of at least one microorganism in or on a material or medium susceptible to attack by the microorganism which comprises the step of adding to the material or medium a composition of the present invention in an amount effective to control the growth of the microorganism.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring or by metering with a suitable device so that a solution or dispersion of the composition can be produced. As these terms are used herein, "preventing" (which includes mitigating) spoilage or effects is to be understood that the present invention in effect "controls" the growth of at least one microorganism, responsible, at least in part, for the spoilage. It is to be further understood that by "controlling" (i.e., preventing), the growth of at least one of these types of microorganisms is inhibited. In other words, there is no growth or essentially no growth of at least one microorganism. "Controlling" the growth of at least one microorganism maintains the microorganism population at a desired level, reduces the population to a desired level (even to undetectable limits, e.g., zero population), and/or inhibits the growth of the microorganism. Thus, the substrates or materials susceptible to attack by these types of microorganisms are preserved from this attack and the resulting spoilage or other detrimental effects caused by the microorganisms. Further, it is to be understood that "controlling" the growth of at least one microorganism also includes biostatically reducing and/or maintaining a low level of microorganisms such that the attack by microorganisms and any resulting spoilage or other detrimental effects are mitigated, i.e., the microorganism growth rate or microorganism attack rate is slowed down or eliminated.

Microorganisms, as used herein, include, but are not limited to bacteria, (both gram-positive and-negative), fungi, algae, viruses, amoebae, spores, and the like, and include both yeast and molds.

Preferably, at least an equimolar portion of the chosen amino acid is used in preparing the solution, preferably in excess of the sequester univalent metal ions (e.g., Ag); at least twice as much for bivalent metals (e.g. Cu), and so on. Any source of ionic M in the form of salts can be used in the present invention. For the case of silver, colloidal silver can be used as well.

The aqueous solution may be condensed and dried using conventional methods available to those skilled in the art to produce gels, tablets, or powders.

The biocides or microbicidal compositions of the present invention described herein have a plethora of applications and uses. They are suitable for the sterilization of drinking water, suitable for the beverage and food industry, suitable for sterilizing exposed surfaces, exhaust air and ventilation components, animal feed, suitable for use in the pharmaceutical industry, in hospitals, for surgical equipment, in swimming pools, in saunas, and for fish, poultry, and cattle farming, and the like.

The present invention is also effective in controlling biofouling. The microbicidal formulations of the present invention can be introduced directly into the source of where the biofouling is occurring or can be mixed with aqueous solutions and introduced into the area where biofouling is occurring by employing methods known to those skilled in the art.

Another beneficial use of the present invention is with respect to preserving or extending the life of flowers and plants. The present invention can be used as a preservative for cut flowers and cut plants by including the formulation of the present invention in the water in which the cut flowers or plants are placed into or can be formulated into a powder or tablet which can be introduced into the containing holding the cut flowers or plants. Also, the formulations of the present invention can be used as a spray which is applied to living plants and flowers and acts as an agent to control pests, insects, and/or microorganisms and thus preserves a living plant and protects the plant from plant diseases, bacteria, viruses, fungus, algae, insects, and the like. The amount of the formulation which is used depends upon the plant or flowers and as described above, is typically a diluted aqueous formulation containing the microbicidal compositions of the present invention.

The present invention is further illustrated by the following examples. These experiments constitute some of the embodiments of the invention herein disclosed. After the preparation of these disinfectants according to the present technique, their efficacy with respect to toxicity was then tested and evaluated against a broad spectrum of pathogenic microorganisms.

Methodology

I. Chemical

Under minimum light, and at room temperature, a silver ion solution of $1.1 \times 10^5$ ppm was prepared by dissolving 400 mg of silver nitrate in 2.045 ml of double distilled-deionized water and 0.255 ml of 85% phosphoric acid. This solution was then used for the proceeding experiments.

EXAMPLE 1

Preparation of Silver-glutamic Acid Complex

By using a micropipet, 230 $\mu$l of the above prepared solution was placed in a microtube where 34.61 mg of glutamic acid was added, and the mixture was stirred thoroughly. This amount of glutamic acid represents an equimolar amount of amino acid with respect to the silver ions in the above prepared solution. Instantly, an insoluble material was observed. This insoluble dispersant has microbial killing activities. This prepared solution was then mixed with 50 ml of double distilled-de-ionized water. The solution was mixed continuously until homogenization was achieved. Then, the product was poured into a dark bottle. This desired product can be added to or proportioned into aqueous systems and diluted to achieve the required germicidal potency, depending on its intended use.

EXAMPLE 2

Preparation of Silver-Leucine Complex

The same procedure in Example 1 above was duplicated, but the amino acid used was leucine instead of glutamic acid. The amount of leucine used in this case was 30.84 mg which again represents an equimolar amount of the amino acid with respect to the silver ions.

EXAMPLE 3

Preparation of Silver-Arginine Complex

The same procedure from Example 1 was again repeated, but the amino acid used was arginine. The amount of arginine used in this case was 40.97 mg which again represents an equimolar amount.

To study the effect of hydrogen peroxide on increasing the potency of these disinfectants, the three prepared solutions (Example I–III) were mixed with 50 ml of 50% $H_2O_2$ rather than water. Again, these prepared solutions were poured into dark bottles.

II. Biological

1. Efficacy of Examples 1–3 Disinfectant

The above concludes the preparation of these disinfectants. However, to utilize these mixtures as bactericides, 5 ml of each bottled solution was added to 45 ml of double distilled-de-ionized water (10% by volume). Without the presence of $H_2O_2$, this constitutes an active concentration of about 51 ppm of complex silver which proved to be sufficient to readily kill bacteria. The upper and lower concentration limits may be different if desired, depending on the nature of the desired application. For the samples where $H_2O_2$ is present, the active concentration of the disinfectant should be around 56,000 ppm.

The diluted solutions were then tested on several kinds of actively growing pathogenic bacteria to ascertain their effectiveness. Different strains of pathogenic bacteria were employed for the testing; namely, *E. coli, Stafelococus, Bascillus*, and *Salmonella*. For all the bacteria used, the microbial killing activity was readily observed. The arginine-complex showed the most potency followed by the leucine-complex, and finally the glutamic acid-complex.

With respect to the presence of $H_2O_2$ in relation to its absence, the difference on the average was roughly around 3 times greater even though the active concentration was almost 1098 times greater than that for the case of an absence of $H_2O_2$. The difference in biocidal activity is not reflected in this value (1098 times greater while the increase is tripled). This is indicative that the biocidal activity is almost solely due to the R-M complex of the present invention. The order of efficacy with respect to the amino acid used was the same as when $H_2O_2$ was absent.

3. Organo-Metallic Disinfectant or Preservative for Cut Flowers and Plants

A sample was prepared in accordance with the procedure described in Example 1, where the resultant disinfectant was diluted with tap water, and was used to study its effects on the preservation of cut flowers and plants. A silver concentration of approximately 166 ppb was used. Both inoculated and controlled samples were tested in which freshly-cut roses were placed in the prepared solution and tap water, respectively. Cut roses were chosen because they are very susceptible to slight changes in the surrounding area and are equally susceptible to chemicals. For comparative purposes, other preservative type chemicals were also tested; namely, silver thiosulfate and hypochlorite.

All the samples were examined after 15 days, and it was found that the present invention is far more superior than all the other chemicals used, including the controlled samples, in that there were no black or brown burns on the petals and there were no wilted flowers, and the stems and leaves were in good condition. In the case of the two other chemicals used, it was observed that there was discoloration of the petals, loss of leaves and petals, and dehydration.

III. Structural Analysis of Microbicide

Following the procedure described in Example 1, a sample of silver-glutamic acid complex was prepared and analyzed as follows:

Under minimum light, and at room temperature, an aliquot of silver ion solution of $1.1 \times 10^5$ ppm was prepared by dissolving 2.0 g of silver nitrate in 10.225 ml of doubled distilled-de-ionized water and 1.275 ml of 85% $H_3PO_4$. Following that, on an equimolar basis with respect to silver, 1.73 g of glutamic acid was added to the solution where the solution was thoroughly mixed and homogenized. Instantly, a yellowish-tan insoluble precipitate was observed. The liquid of the aqueous amino acid/silver sample was then decanted from the yellowish-tan solid. The solid was dried in an oven. This sample was submitted for structural analyses of the precipitates.

A. DSC Analyses: (Perkin-Elmer/DSC Series 7)

DSC is a technique used to analyze material when heated. It is used to study the thermal transitions of a certain material as functions of temperatures and heat flows. Such measurements provide quantitative as well as qualitative information about the chemical, i.e., melting point temperature and heat of melting, glass transition temperature, crystallization studies, and identification of phase transformation.

Accordingly, three events were observed: the first two were exothermic transitions at 184° C. and 250° C. The last occurrence was an endothermic melting transition at 352° C. This is depicted in FIG. 1.

B. NMR Analyses:

Nuclear Magnetic Resonance Spectroscopy (NMR) is an important method for material characterization. The importance of NMR arises in part because the signal can be assigned to specific atoms. The properties of NMR signals depend on the magnetic environment of the NMR active nuclei and the local fields they experience. Since the NMR spectrum is determined by local forces, this method provides valuable information at an atomic scale.

Another portion of this solid was subjected to NMR studies using Bruker/AC270. It was found, however, that this material was insoluble in water (acid), dimethylsulfoxide, tetrahydrofuran, and dimethylformamide. Another portion of this solid was then mixed with dilute sodium deuteroxide (NaOD) in deuterium oxide ($D_2O$). The yellowish-tan solid soon turned black as the silver "crashed out" the solution. The resulting mixture was subjected to proton and carbon NMR analyses; this is shown in FIGS. 2 and 3, respectively. Characteristic resonances of the amino acid, which was glutamic acid, were observed.

In the proton NMR spectrum (FIG. 2), the glutamic resonances were found at 3.07 (dd, —$CH_2C\underline{H}(NH_2)C(O)$—), 2.04 (t, —$CH_2C\underline{H}_2C(O)$—) and 1.66 (m, —$CH_2C\underline{H}_2CH$—) ppm. The $^{13}C$ NMR spectrum (FIG. 3) confirmed the presence of glutamic acid with resonances at 185.01 ($HOC_\delta(O)$—), 36.31 (—$CH_2C_\gamma H_2C(O)$—), 33.98 (—$CH_2C_\beta H_2CH$—), and 58.10 (—$CH_2C_\alpha H(NH_2)C(O)$—) ppm. However, the other carbonyl resonance was not observed. Thus, the sample appears to be comprised of glutamic acid coordinated to silver.

C. Results

As stated earlier, the DSC results show two exothermic transition states (troughs) and one endothermic melting transition state (peak), FIG. 1. Careful examination of FIG. 1 reveals some interesting and novel features: A) this material appears not to exhibit a glass transition state which is only observed for amorphous materials (materials whose chains are not arranged in an orderly manner, but are just strewn around in any fashion; i.e., random) because the DSC profile is smooth and lacking a sudden jump in temperature and heat flow which is a signature of this state; B) since only exothermic transition states were observed, there appears to be no glass transition state, and the material may be composed of crystals only, and therefore maybe in a crystalline state (materials that are arranged in an orderly manner); and C) two exothermic states appear to take place at two distinct temperatures at 184° C. and 250° C. This is somewhat unusual since it may imply that there are may be two distinct crystalline structures with two different crystalline temperatures in the material, or there may be chemical interactions that are taking place such as a decomposition, or chemical reactions.

The proton NMR provided in FIG. 2 shows three different resonances. Several of these protons are enantiotopic, due to the chiral center of glutamic acid, which in turn complicates the spectrum. The two carboxylic acid protons are not observed since the experiment was conducted in deuterated water.

The $^{13}$C spectrum shown in FIG. 3 appears to confirm the presence of glutamic acid. However, the fact that the other carbonyl carbon was not observed, and possibly the silver may have distorted and/or disrupted this bond.

On the bases of the above experimental observations, it can be seen that such complexes demonstrate novel and peculiar structural characteristics and features.

Although the present invention has been described with reference to certain preferred embodiments, other variations are possible. Therefore, the spirit and scope of the appended claims should not be limited to the description contained herein.

The previous explanation and the illustrations and procedures set forth above are solely intended for the purpose of setting out the generic and general embodiments of the present invention. Therefore, it is to be understood that the present invention by no means is limited to the specific features disclosed herein, and such details can be varied by those skilled in the art in consideration of the present specification and practiced without departing from the true scope and merits of the invention.

Having thus described the present invention, the true scope and spirit of it is therefore presented by the following claims:

What is claimed is:

1. A microbicidal formulation comprising at least one disinfectant and a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is an amino acid, wherein said amino acid is selected as forming a complex with M at a pH of 2 or less, wherein said amino acid includes a double bonded oxygen, wherein said double bonded oxygen of said amino acid is complexed to M at a pH of 2 or less, and wherein said disinfectant and said complex are not the same, and wherein said complex is a solid in said formulation.

2. The microbicidal formulation of claim 1, wherein the mirobicidal formulation is mixed with an aqueous solution.

3. The microbicidal formulation of claim 2, wherein said microbicidal formulation is mixed in said aqueous solution at a concentration of from about 0.0010%, to about 10% by total volume.

4. The microbicidal formulation of claim 1, wherein said at least one metal ion is a silver ion or colloidal silver or both.

5. The microbicidal formulation of claim 1, wherein said at least one metal ion is copper, zinc, mercury, chromium, manganese, nickel, cadmium, arsenic, cobalt, aluminum, lead, selenium, platinum, gold, titanium, tin, barium, vanadium, bismuth, iron, strontium, antimony, or combinations thereof.

6. The microbicidal formulation of claim 1, wherein said at least one organic chelating moiety is formed from an alpha-amino acid.

7. The microbicidal formulation of claim 1, wherein said at least one organic chelating moiety is isoleucine, phenylalanine, leucine, lysine, threonine, tryptophan, valine, alanine, arginine, histidine, or mixtures thereof.

8. The microbicidal formulation of claim 1, wherein the molar ratio of R to M is from about 1:1 to about 2:1.

9. The microbicidal formulation of claim 1, wherein said at least one disinfectant comprises one or more of chlorhexidine gluconate, chlorhexidine digluconate, chlorhexidine dihydrochloride, and chlorhexidine diacetate.

10. The microbicidal formulation of claim 1, wherein said at least one disinfectant comprises isopropyl alcohol or hydrogen peroxide, or both.

11. The microbicidal formulation of claim 1, further comprising artificial or natural colors or flavors.

12. The microbicidal formulation of claim 1, wherein said formulation is a gel or solid.

13. A method to control biofouling in a system, comprising introducing an effective amount of said microbicidal formulation of claim 1 to said system to control said biofouling.

14. A microbicidal formulation comprising at least one disinfectant and a product obtained by combining at least one metal ion (M) with at least an equimolar amount of at least one organic chelating moiety (R) based on the amount of M, wherein M is microbicidal to at least one microorganism, wherein said at least organic chelating moiety is an amino acid, wherein said amino acid is selected as forming a complex with M at a pH of 2 or less, wherein said amino acid includes a double bonded oxygen, wherein said double bonded oxygen of said amino acid is complexed to M at a pH of about 2 or less, and wherein said disinfectant and said product are not the same.

15. The microbicidal formulation of claim 14 wherein said at least one metal ion is a silver ion or colloidal silver.

16. A method to control the growth of a microorganism susceptible to treatment with a metal ion, said method comprising:

treating said microorganism with the microbicidal formulation of claim 14.

17. A method of controlling biofouling in a system, comprising introducing to said system an effective amount of the microbicidal formulation of claim 14.

18. A method to control the growth of microorganisms comprising contacting the microorganisms with a microbicidal formulation comprising a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is an amino acid, wherein said amino acid is selected as forming a complex with M at a pH of 2 or less, wherein said amino acid includes a double bonded oxygen, wherein said double bonded oxygen of said amino acid is complexed to M at a pH of about 2 or less, and wherein said microbicidal composition kills said microorganisms intracellularly.

19. A method to prepare a microbicidal formulation comprising at least one disinfectant and a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is an amino acid, wherein said amino acid is selected as forming a complex with M at a pH of 2 or less, wherein said amino acid includes a double bonded oxygen, and wherein said double bonded oxygen of said amino acid is complexed to M and wherein said disinfectant and said complex are not the same, wherein said method comprises dissolving a salt containing metal in at least one inorganic acid and an aqueous source;

adding at least one organic chelating compound containing R to form a metal complex having the formula R-M, wherein the preparation of the formulation occurs at a pH of about 2.0 or less and combining the complex with the at least one disinfectant.

20. A microbicidal formulation comprising a disinfectant and a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is formed from an amino acid, wherein said amino acid is selected as forming a complex with M at a pH of 2 or less, said organic chelating moiety has a carboxylic group which forms a dative covalent bond with M, wherein said carboxylic group includes a double bonded oxygen which is complexed to M at a pH of about 2 or less, and wherein said disinfectant and said complex are not the same.

21. The microbicidal formulation of claim 20, wherein M is complexed through the doubled bonded oxygen of the carboxylic group.

22. A method for preserving cut flowers or plants from pathological microorganisms comprising:

treating said flowers and plants with the microbicidal formulation comprising a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is an amino acid, wherein said amino acid is selected as forming a complex with M at a pH of 2 or less, wherein said amino acid includes a double bonded oxygen, and wherein said double bonded oxygen of said amino acid is complexed to M at a pH of about 2 or less.

23. The method of claim 22, wherein the flowers and plants are treated by immersing a portion of the flower or plant in a mixture of the microbiocidal formulation and an aqueous solution.

24. The method of claim 22, wherein the flowers and plants are sprayed with a mixture of the microbiocidal formulation and an aqueous solution.

25. The method of claim 22, wherein the flowers or plants are treated by introducing into a container of water a tablet comprising the microbicidal formulation.

26. A method for protecting living flowers or plants comprising treating said flowers and plants with the microbicidal formulation comprising a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is an amino acid, wherein said amino acid is selected as forming a complex with M at a pH of 2 or less, wherein said amino acid includes a double bonded oxygen, and wherein said double bonded oxygen of said amino acid is complexed to M at a pH of about 2 or less.

27. A microbicidal formulation comprising an organometallic chelate of silver cations and glutamic acid, wherein the chelate exhibits the structural spectra depicted in FIGS. 1, 2, or 3.

\* \* \* \* \*

UNITED STATES PATENT AND TRADEMARK OFFICE
CERTIFICATE OF CORRECTION

PATENT NO. : 6,939,566 B2 Page 1 of 1
APPLICATION NO. : 09/761561
DATED : September 6, 2005
INVENTOR(S) : Batarseh et al.

It is certified that error appears in the above-identified patent and that said Letters Patent is hereby corrected as shown below:

ON THE COVER:

(63) "PCT/US00/10665, filed on Apr. 20, 1999." should read -- PCT/US00/10665, filed on Apr. 19, 2000.--

IN THE SPECIFICATION:

Column 1, line 12, "Apr. 20, 1999" should read --Apr. 19, 2000--.

Signed and Sealed this

Eleventh Day of July, 2006

JON W. DUDAS
*Director of the United States Patent and Trademark Office*